United States Patent
Houser

(10) Patent No.: US 10,314,607 B2
(45) Date of Patent: Jun. 11, 2019

(54) ULTRASONIC SURGICAL INSTRUMENT WITH TUBULAR ACOUSTIC WAVEGUIDE SEGMENT

(71) Applicant: Ethicon Endo-Surgery, LLC, Guaynabo, PR (US)

(72) Inventor: Kevin L. Houser, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 470 days.

(21) Appl. No.: 14/976,047

(22) Filed: Dec. 21, 2015

(65) Prior Publication Data

US 2017/0172607 A1 Jun. 22, 2017

(51) Int. Cl.
  *A61B 17/32* (2006.01)
  *A61B 17/28* (2006.01)
  *A61B 18/00* (2006.01)

(52) U.S. Cl.
  CPC ...... *A61B 17/320068* (2013.01); *A61B 17/28* (2013.01); *A61B 17/320092* (2013.01); *A61B 2017/2825* (2013.01); *A61B 2018/00601* (2013.01); *A61B 2018/00607* (2013.01)

(58) Field of Classification Search
  CPC ............ A61B 17/22004; A61B 17/225; A61B 17/320068; A61B 17/320092; A61B 2017/320094; A61F 9/00745
  USPC ........................................................ 606/169
  See application file for complete search history.

(56) References Cited

U.S. PATENT DOCUMENTS

| 5,318,570 A * | 6/1994 | Hood ................. A61B 17/8847 |
| | | 601/2 |
| 5,322,055 A | 6/1994 | Davison et al. |
| 5,324,299 A | 6/1994 | Davison et al. |
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |

(Continued)

FOREIGN PATENT DOCUMENTS

WO    WO 2007/143439 A2    12/2007

OTHER PUBLICATIONS

U.S. Appl. No. 61/410,603, filed Nov. 5, 2010.
International Search Report and Written Opinion dated Apr. 6, 2017 for Application No. PCT/US2016/066473, 10 pgs.

*Primary Examiner* — Melanie R Tyson
(74) *Attorney, Agent, or Firm* — Frost Brown Todd LLC

(57) ABSTRACT

An ultrasonic instrument includes a body and a shaft assembly extending distally from the body. The shaft assembly includes an acoustic waveguide. The instrument further includes an end effector including an ultrasonic blade. The ultrasonic blade is in acoustic communication with the acoustic waveguide. The ultrasonic blade is defined by a solid core shaft of a material or combination of materials. At least a portion of the acoustic waveguide comprises a hollow tubular member coupled with the solid core shaft.

20 Claims, 5 Drawing Sheets

(56) References Cited

U.S. PATENT DOCUMENTS

| | | |
|---|---|---|
| 7,189,233 B2 | 3/2007 | Truckai et al. |
| 7,220,951 B2 | 5/2007 | Truckai et al. |
| 7,296,318 B2 | 11/2007 | Mourad et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,544,200 B2 | 6/2009 | Houser et al. |
| 8,057,498 B2 | 11/2011 | Robertson |
| 8,461,744 B2 | 6/2013 | Wiener et al. |
| 8,591,536 B2 | 11/2013 | Robertson |
| 8,623,027 B2 | 1/2014 | Price et al. |
| 8,663,220 B2 | 5/2014 | Wiener et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0030311 A1* | 1/2009 | Stulen ............ A61B 17/320092 600/439 |
| 2009/0270891 A1* | 10/2009 | Beaupre ......... A61B 17/320092 606/169 |
| 2012/0112687 A1 | 5/2012 | Houser et al. |
| 2012/0116265 A1 | 5/2012 | Houser et al. |
| 2014/0005701 A1 | 1/2014 | Olson et al. |
| 2015/0073457 A1* | 3/2015 | Stoddard ........ A61B 17/320092 606/169 |
| 2015/0080924 A1 | 3/2015 | Stulen et al. |
| 2015/0141981 A1 | 5/2015 | Price et al. |

\* cited by examiner

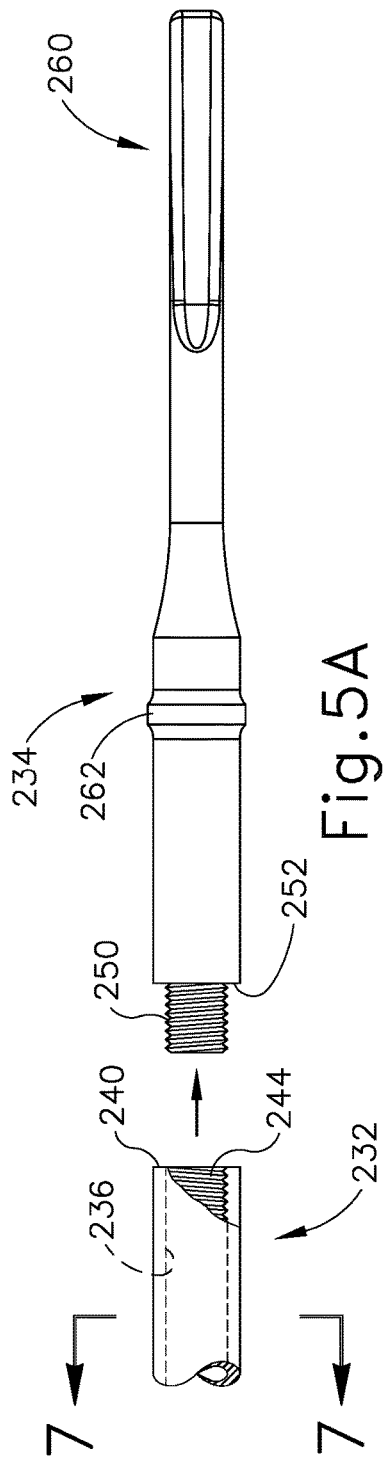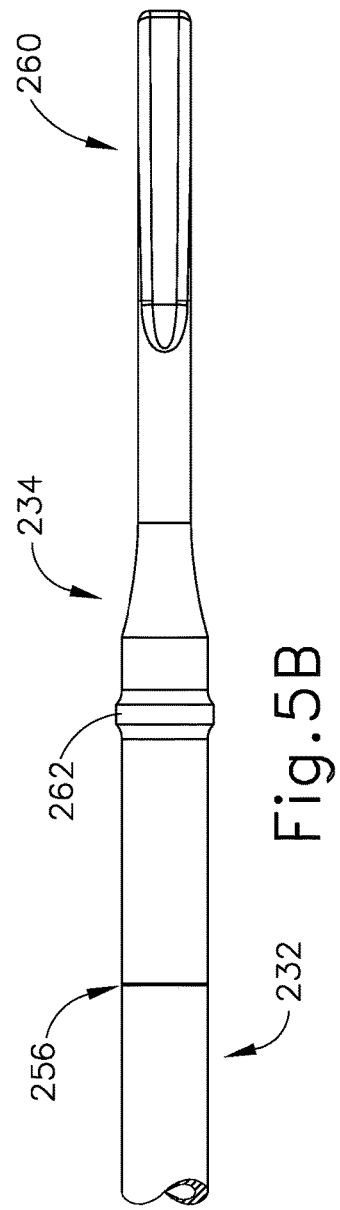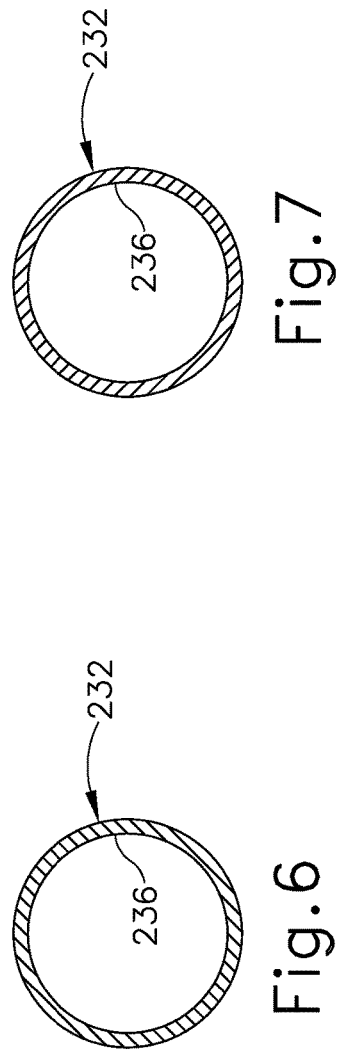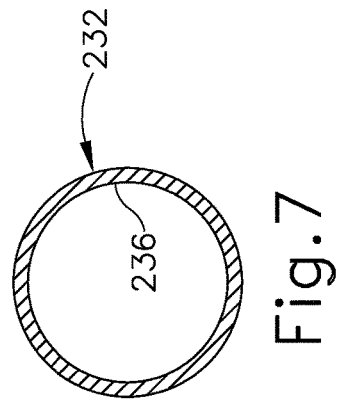

ULTRASONIC SURGICAL INSTRUMENT WITH TUBULAR ACOUSTIC WAVEGUIDE SEGMENT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pat. No. 7,544,200, entitled "Combination Tissue Pad for Use with an Ultrasonic Surgical Instrument," issued Jun. 9, 2009, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, now abandoned, entitled "Ultrasonic Waveguide and Blade," published Dec. 6, 2007, the disclosure of which is incorporated by reference herein; U.S. Pub. No. 2008/0200940, now abandoned, entitled "Ultrasonic Device for Cutting and Coagulating," published Aug. 21, 2008, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use,"

issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pat. No. 8,663,220, entitled "Ultrasonic Electrosurgical Instruments," issued March 4, 2014, the disclosure of which is incorporated herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5A depicts a detailed unassembled view of a distal portion of the waveguide of FIG. 3;

FIG. 5B depicts a detailed assembled view of the distal portion of the waveguide shown in FIG. 5A;

FIG. 6 depicts a cross-sectional view of the waveguide of FIG. 3, taken along line 6-6 of FIG. 4A; and FIG. 7 depicts a cross-sectional view of the waveguide of FIG. 3, taken along line 7-7 of FIG. 5A.

Figure 1:
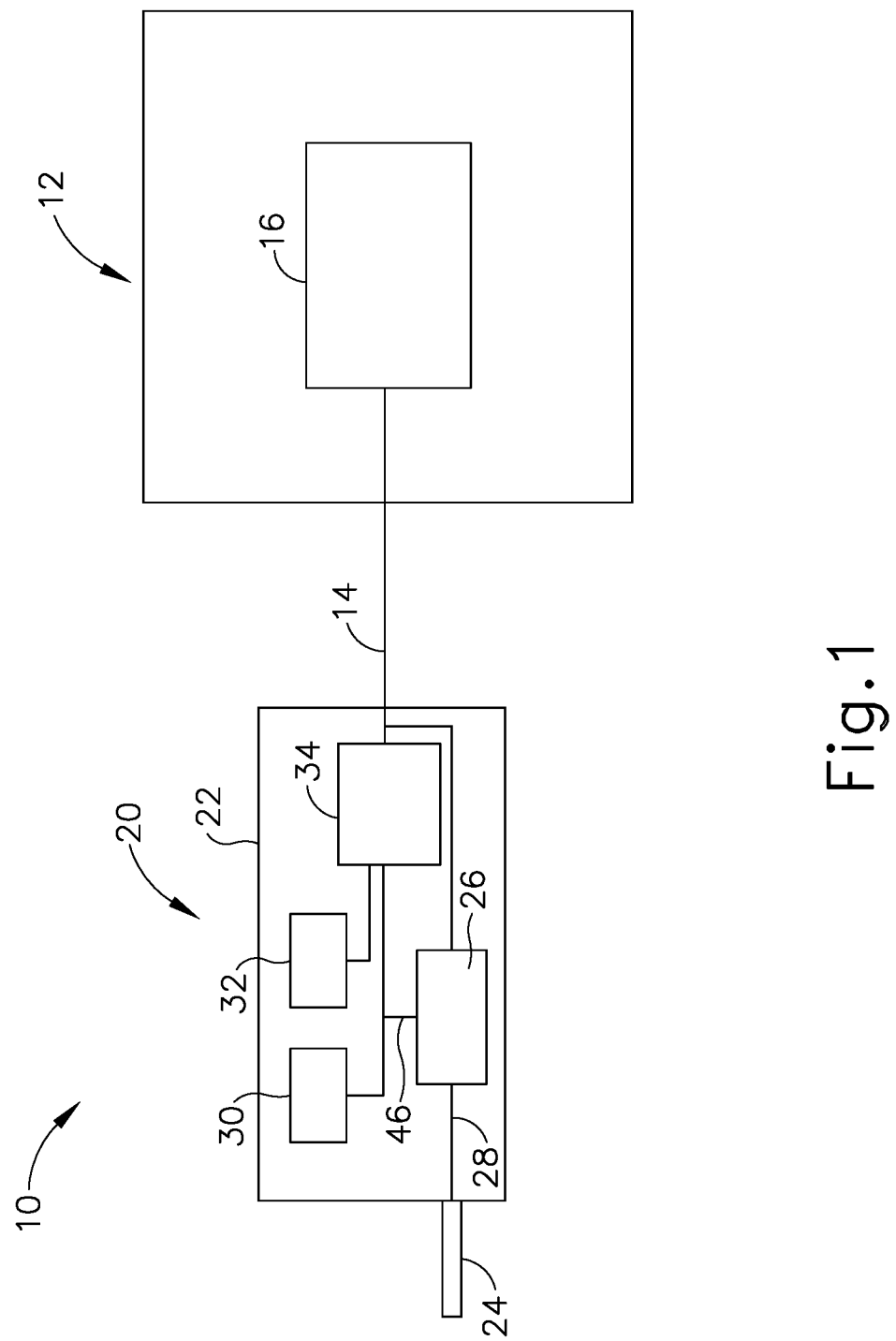
FIG. 1 depicts a block schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. OVERVIEW OF EXEMPLARY ULTRASONIC SURGICAL SYSTEM

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials. In the present example, waveguide (28) is a unitary component.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. OVERVIEW OF EXEMPLARY ULTRASONIC SURGICAL INSTRUMENT

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
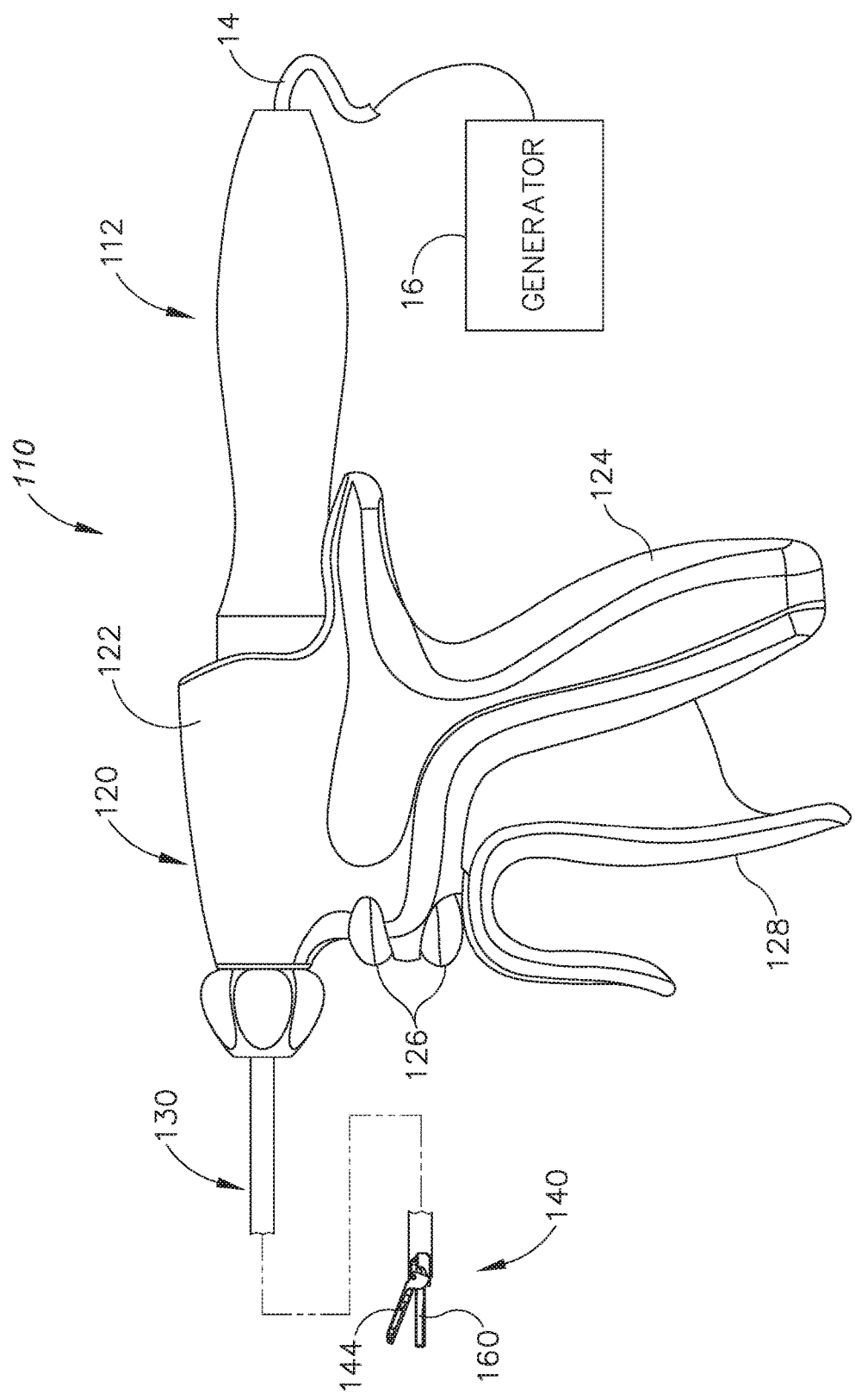
FIG. 2 depicts a side elevational view of an exemplary form that the instrument of FIG. 1 may take.

FIG. 2 illustrates an exemplary ultrasonic surgical instrument (110). At least part of instrument (110) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 8,461,744; U.S. Pub. No. 2009/0105750, issued as U.S. Pat. No. 8,623,027 on Jan. 7, 2014; U.S. Pat. No. 7,544,200; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,71 on May 5, 2015; U.S. Pub. No. 2012/0112687, issued as U.S. Pat. No. 9,095,367 on Aug. 4, 2105; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. pat. app. Ser. No. 14/028,717, issued as U.S. Pat. No. 10,172,636 on Jan. 8, 2019; and/or U.S. pat. app. Ser. No. 61/410,603. The disclosures of each of the foregoing patents, publications, and applications are incorporated by reference herein. As described therein and as will be described in greater detail below, instrument (110) is operable to cut tissue and seal or weld tissue substantially simultaneously. It should also be understood that instrument (110) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (110) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (110), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is pivotably coupled with an inner tube and an outer tube that form shaft assembly (130). Such an inner and outer tube configuration may be provided in accordance with the teachings of various references that are cited herein. Clamp arm (144) is further coupled with trigger (128). Trigger (128) is operable to drive one of the tubes of shaft assembly (130) longitudinally while the other tube of shaft assembly (130) remains stationary. This relative longitudinal movement between the tubes of shaft assembly (130) provides pivotal movement of clamp arm (144). Clamp arm (144) is thus pivotable toward ultrasonic blade (160) in response to pivoting of trigger (128) toward pistol grip (124); and clamp arm (144) is pivotable away from ultrasonic blade (160) in response to pivoting of trigger (128) away from pistol grip (124). Clamp arm (144) is thereby operable to cooperate with ultrasonic blade (160) to grasp and release tissue; and clamp arm (144) is further operable to compress tissue against ultrasonic blade (160) to thereby enhance the communication of ultrasonic vibration from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (136) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (44) and blade (160). In particular, activation of a second one of the buttons (136) may cause vibration of ultrasonic blade (160) at a relatively high amplitude. Other suitable operational modes that may be associated with buttons (126) will be apparent to persons skilled in the art in view of the teachings herein.

In some versions, end effector (140) is further operable to apply radiofrequency (RF) electrosurgical energy to tissue that is captured between clamp arm (144) and blade (160). By way of example only, end effector (140) may include a single electrode that cooperates with a conventional ground pad that is secured to the patient, such that end effector (140) applies monopolar RF electrosurgical energy to the tissue. As another merely illustrative example, clamp arm (144) may include two electrodes that are operable to apply bipolar RF electrosurgical energy to the tissue. As yet another merely illustrative example, clamp arm (144) may include a single electrode and ultrasonic blade (160) may serve as a return path, such that ultrasonic blade (160) cooperates with the electrode of clamp arm (144) to apply bipolar RF electrosurgical energy to the tissue. In addition to or as an alternative to the foregoing, end effector (140) may be constructed and operable in accordance with at least some of the teachings of U.S. Pat. No. 8,663,220, entitled "Ultrasonic Electrosurgical Instruments," issued Mar. 4, 2014, the disclosure of which is incorporated by reference herein. Other suitable arrangements will be apparent to those of ordinary skill in the art in view of the teachings herein.

Instrument (110) may provide the operator with various ways in which to selectively apply only ultrasonic energy to tissue via end effector (140), only RF electrosurgical energy to tissue via end effector (140), or some combination of ultrasonic energy and RF electrosurgical energy to tissue via end effector (140). In versions where end effector (140) is operable to apply a combination of ultrasonic energy and RF electrosurgical energy to tissue, end effector (140) may be configured to apply ultrasonic energy and RF electrosurgical energy to tissue simultaneously. In addition or in the alternative, in versions where end effector (140) is operable to apply a combination of ultrasonic energy and RF electrosurgical energy to tissue, end effector (140) may be configured to apply ultrasonic energy and RF electrosurgical energy to tissue in a sequence. Such a sequence may be predetermined; or may be based on sensed tissue conditions (e.g., tissue temperature, density, thickness, etc.). Various suitable control algorithms that may be used are disclosed in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. It should also be understood that the control of ultrasonic energy and RF electrosurgical energy may be provided in accordance with at least some of the teachings of U.S. Pat. No. 8,663,220, entitled "Ultrasonic Electrosurgical Instruments," issued Mar. 4, 2014, the disclosure of which is incorporated by reference herein.

III. EXEMPLARY ALTERNATIVE WAVEGUIDE

Conventional waveguides (28) may be formed of a solid core of material. This construction may require surface features to be formed using a lathe and/or milling process, which may result in wasted material. In addition to providing a time consuming manufacturing process, this may also be costly with respect to the loss of material that is removed from a block of material during the formation process. It may therefore be desirable to provide a construction of waveguide (28) that enables waveguide (28) to be formed more efficiently, reducing the amount of material that may be lost during the manufacturing process.

FIGS. 3-5B show an exemplary alternative waveguide (228) that may be readily incorporated into instrument (20, 110), particularly, into an acoustic drivetrain of instrument (20, 110). Waveguide (228) thus represents an alternative form that waveguide (28) may take. Waveguide (228) of the present example includes a blade (260) that is operable to vibrate at ultrasonic frequencies in order to effectively cut through and seal tissue, particularly when the tissue is being compressed between blade (260) and another portion of an end effector, such as clamp arm (144) of end effector (140). It should be understood that the proximal end of waveguide (228) may be coupled with transducer assembly (112) to receive the ultrasonic vibrations that are ultimately applied to tissue via blade (260). As shown, rather than being a solid, unitary member, waveguide (228) of this example comprises a proximal portion (230), a middle portion (232), and a distal portion (234). As discussed in further detail below, middle portion (232) is configured to be removably coupled to proximal portion (230) and distal portion (234) to form waveguide (228).

Figure 4A:
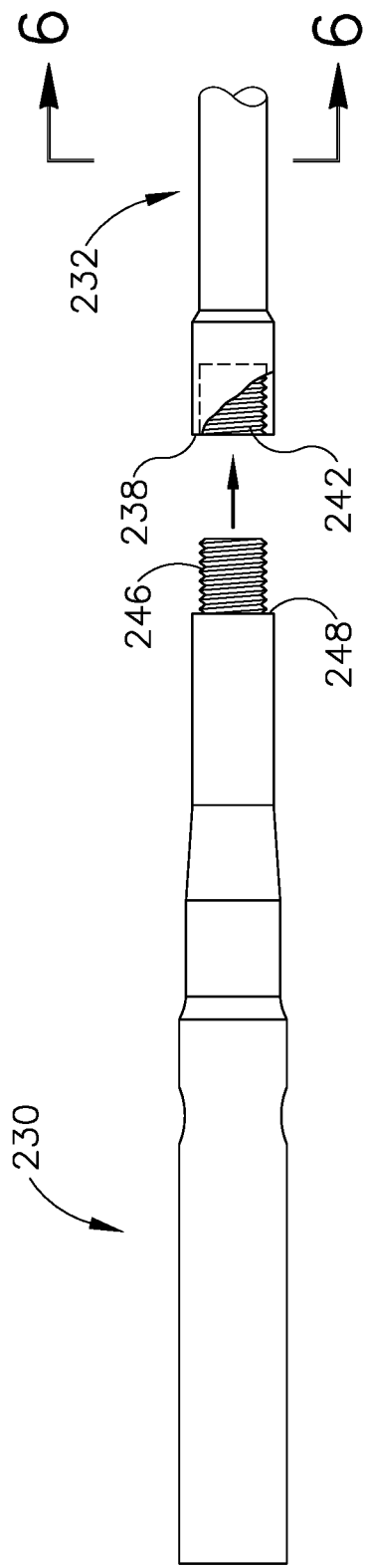
FIG. 4A depicts a detailed unassembled view of a proximal portion of the waveguide of FIG. 3.

In the present example, proximal portion (230) and distal portion (234) are configured substantially in accordance with waveguide (28). That is, proximal and distal portions (230, 234) are solid core shaft members constructed out of a material or combination of materials. As shown, however, middle portion (232) is constructed from a hollow tube of material or combination of materials. Particularly, and as best seen in FIGS. 6-7, middle portion (232) is a tubular member that includes a lumen (236) extending continuously between a first, proximal end (238) and a second, distal end (240) of the middle portion (232). Thus, in the example shown, middle portion (232) has a lower average density than the proximal and distal portions (230, 234). Lumen (236) includes a first female threaded portion (242) at the first end (238) (as seen in FIG. 4A) and a second female threaded portion (244) at the second end (240) (as seen in FIG. 5A). As shown in FIG. 4A, proximal portion (230) includes a first male threaded portion (246) and a contact surface (248) adjacent to first male threaded portion (246). In other words, first male threaded portion (246) essentially extends distally from the aspect of proximal portion (230) that defines contact surface (248). Similarly, as shown in FIG. 5A, distal portion (234) includes a second male threaded portion (250) and a contact surface (252) adjacent to male threaded portion (250). In other words, second male threaded portion (250) extends proximally from the aspect of distal portion (234) that defines contact surface (252).

Figure 4B:
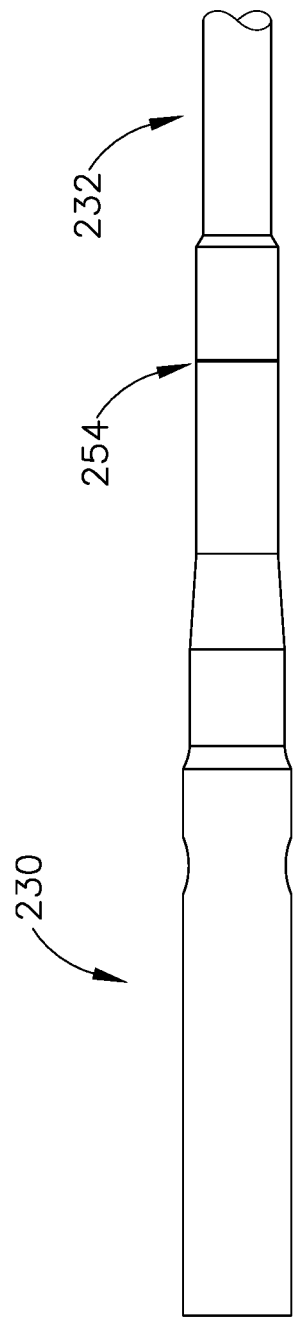
FIG. 4B depicts a detailed assembled view of the proximal portion of the waveguide shown in FIG. 4A.

As shown in FIGS. 4B and 5B, in order to assemble waveguide (228), first male threaded portion (246) may be threadably engaged with first female threaded portion (242) until contact surface (248) abuts first end (238) of middle portion (232). Thus, in the present example, there is no gap at the junction (254) between proximal and middle portions (230, 232). As shown in FIG. 5B, second male threaded portion (250) may be threadably engaged with second female threaded portion (244) until contact surface (252) abuts second end (240) of middle portion (232). Thus, in the present example, there is no gap at the junction (256) between middle and distal portions (232, 234).

In alternative examples, rather than being threadably engageable, proximal and middle portions (230, 232) and/or middle and distal portions (232, 234) may be configured to couple to one another in another manner, such as press fitting. Other suitable manners of mechanically coupling proximal and middle portions (230, 232) and middle and distal portions (232, 234) will be apparent to persons skilled in the art in view of the teachings herein. Moreover, while in the present example there is no gap at the junction (254) between proximal and middle portions (230, 232) when they are coupled to one another, in other examples there may be a gap therebetween. Similarly, in other examples, there may be a gap at the junction between middle and distal portions (232, 234) when they are coupled to one another. As yet another merely illustrative alternative, the distal end of first male threaded portion (246) may engage the distal end of the cavity in first female threaded portion (242), thus forming the abutting surfaces to communicate ultrasonic vibrations, such that first end (238) and contact surface (248) do not contact each other. Other suitable configurations of proximal, middle, and distal portions (230, 232, 234) will be apparent to persons skilled in the art in view of the teachings herein.

In the present example, the acoustic drivetrain includes transducer assembly (112) and acoustic waveguide (228). Various suitable ways in which waveguide (280) may be mechanically and acoustically coupled with transducer assembly (112) will be apparent to those of ordinary skill in the art in view of the teachings herein. Transducer assembly (112) includes a set of piezoelectric discs (not shown) located proximal to a horn (not shown) of waveguide (280). The piezoelectric discs are operable to convert electrical power into ultrasonic vibrations, which are then transmitted along proximal, middle and distal portions (230, 232, 234) of waveguide (280) to blade (260). By way of example only, this portion of the acoustic drivetrain may be operable in accordance with various teachings of various references that are cited herein.

Figure 3:
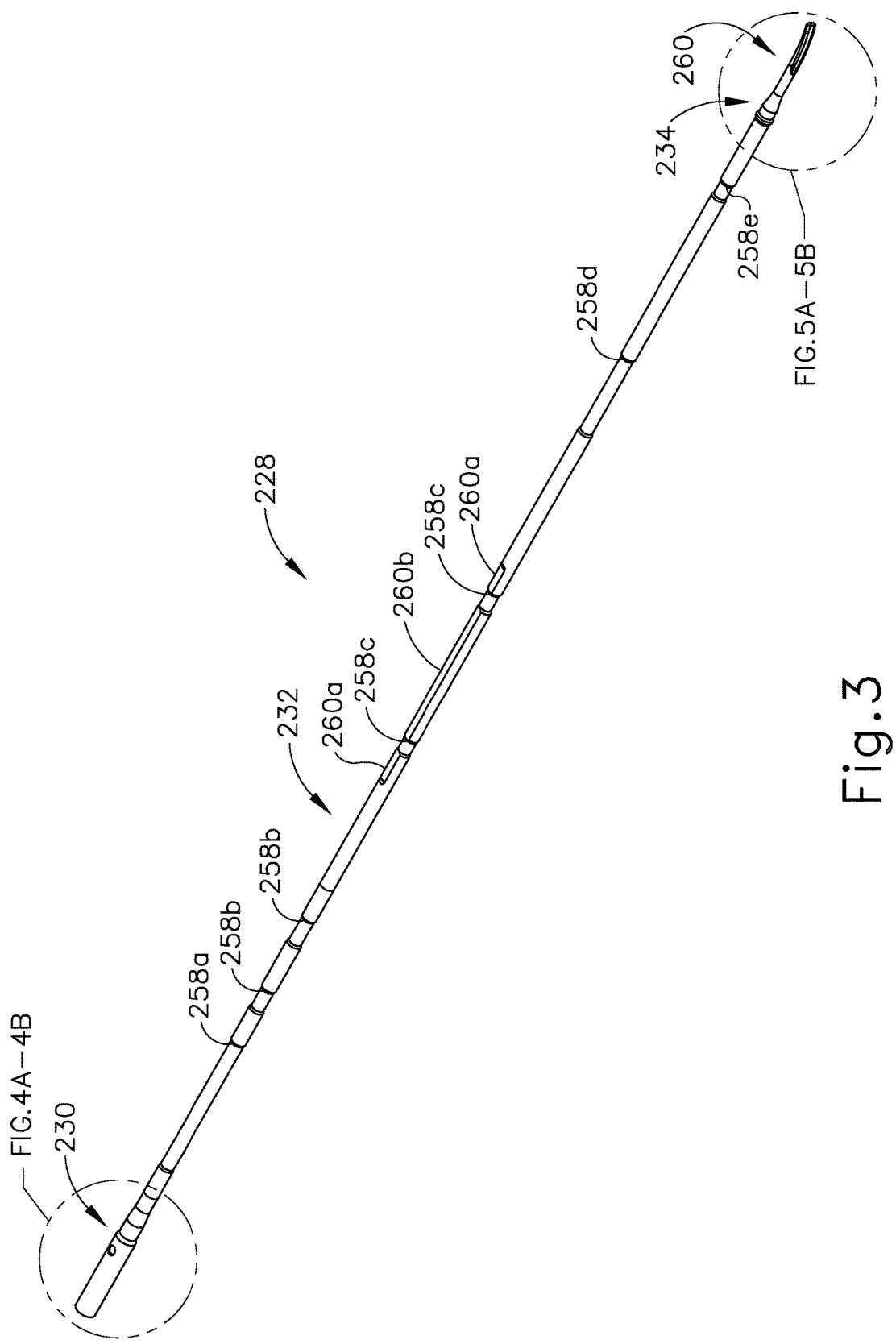
FIG. 3 depicts an exemplary alternative acoustic waveguide that may be incorporated into the instrument of FIG. 2.

It should be understood that waveguide (228) may be configured to amplify mechanical vibrations transmitted through waveguide (228). Furthermore, waveguide (228) may include features operable to control the gain of the longitudinal vibrations along waveguide (228) and/or features to tune waveguide (228) to the resonant frequency of the system. For example, as shown in FIG. 3, waveguide (228) includes a plurality of longitudinally spaced, annular grooves (258a, 258b, 258c, 258d, 258e). In the example shown, groove (258a) has a longer length than groove (258d), which has a longer length than grooves (258b, 258c, 258e). Waveguide (228) further includes opposing pairs of longitudinally spaced notches (260a). The proximal most pair of notches (260a) is positioned adjacent to the proximal most groove (258c), while the distal most pair of notches (260b) is positioned to distal most groove (258c). As shown, waveguide (228) further includes another pair of opposing notches (260b), each of which extend between grooves (258c). Grooves (258a, 258b, 258c, 258d, 258e) and notches (260a, 260b) are provided, at least in part, to assist in controlling the vibratory properties of the waveguide (228).

Waveguide (228) further includes a flange (262). Flange (262) is configured to receive an annular elastomeric seal (not shown). This elastomeric seal may engage the inner wall of an inner tube (not shown) that extends through shaft assembly (130), such that the seal and flange (262) may cooperate to provide structural support to waveguide (228). In other words, the seal and flange (262) may cooperate to prevent waveguide (228) from undesirably deflecting laterally within the inner tube, particularly when blade (260) encounters lateral loads from being pressed against tissue. The seal and flange (262) thus cooperate to prevent waveguide (228) from contacting the inner tube. It should be understood that waveguide (228) may include a series of elastomeric seals that are spaced apart along the length of waveguide (228) for the same purpose, in accordance with configurations that will be apparent to those of ordinary skill in the art in view of the teachings herein.

In the present example, the distal end of blade (260) is located at a position corresponding to an anti-node associated with resonant ultrasonic vibrations communicated through proximal, middle, and distal portions (230, 232, 234) of waveguide (228), in order to tune the acoustic assembly to a preferred resonant frequency $f_o$ when the acoustic assembly is not loaded by tissue. Moreover, each junction (254, 256) is located at a position corresponding to an anti-node associated with resonant ultrasonic vibrations communicated through waveguide (228). In some examples, one or more of threads (240, 244, 246, 250) may be located at a position corresponding to an anti-node associated with resonant ultrasonic vibrations communicated through waveguide (228). However, in other examples, junctions (254, 256) and/or threads (240, 244, 246, 250) may be at a position corresponding to a node associated with resonant ultrasonic vibrations communicated through waveguide (228). Unlike junctions (254, 256), flange (262) is located at a position corresponding to a node associated with resonant ultrasonic vibrations communicated through waveguide (228).

When transducer assembly (112) is energized, the distal end of blade (260) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through each portion (230, 232, 234) of waveguide (228) to reach blade (260), thereby providing oscillation of blade (260) at the resonant ultrasonic frequency. Thus, when tissue is secured between blade (260) a clamp pad on clamp arm (144), for example, the ultrasonic oscillation of blade (260) may simultaneously sever the tissue and denature the proteins in adjacent tissue cells, thereby providing a coagulative effect with relatively little thermal spread. In some versions, an electrical current may also be provided through blade (260) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, various suitable ways in which waveguide (228) may be configured will be apparent to those of ordinary skill in the art in view of the teachings herein.

Proximal and distal portions (230, 234), including blade (260), may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials. In the present example, as discussed above, middle portion (232) comprises a hollow tube that in some versions may be constructed of titanium. However, in other examples, middle portion (232) may be constructed out of a material or combination of materials that propagates ultrasonic energy efficiently, but that is different from the material of proximal and distal portions (230, 234), such as aluminum alloys, stainless steel, or any other acoustically compatible material or combination of materials.

Various features of waveguide (228), such as grooves (258a, 258b, 258c, 258d, 258e) and notches (260a, 260b), may be rolled, pressed, or imparted onto waveguide (228) using any suitable forming techniques. It should be understood that the tubular construction of middle portion (232) may make it easier and more efficient to form the structural features such as grooves (258a, 258b, 258c, 258d, 258e) and notches (260a, 260b) than it might otherwise be to form such features in versions where middle portion (232) is constructed of a solid core material. In particular, the hollow nature of middle portion (232) provides room for material deformation, facilitating use of techniques such as pressing, etc., that would not be feasible in settings where middle portion (232) has a solid core. These additional techniques may result in less waste and may further increase efficiency on the process of forming waveguide (228). These additional techniques may also allow middle portion (232) to be formed of materials that are less expensive than the materials that might otherwise be used to form a waveguide (28) that has a solid core, particularly since middle portion (232) does not need to be made of the same material(s) as proximal and distal portions (230, 234).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body; (b) a shaft assembly extending distally from the body, wherein the shaft assembly comprises an acoustic waveguide; and (d) an end effector comprising an ultrasonic blade, wherein the ultrasonic blade is in acoustic communication with the acoustic waveguide, wherein the ultrasonic blade is defined by a solid core shaft of a material or combination of materials; wherein at least a portion of the acoustic waveguide comprises a hollow tubular member coupled with the solid core shaft.

Example 2

The ultrasonic instrument of Example 1, wherein the hollow tubular member is removably coupled to the ultrasonic blade.

Example 3

The ultrasonic instrument of Example 2, wherein the hollow tubular member and ultrasonic blade define a junction when removably coupled to one another, wherein the junction is located at a position corresponding to at an anti-node associated with resonant ultrasonic vibrations communicated through the waveguide.

Example 4

The ultrasonic instrument of any one or more of Examples 2 through 3, further comprising a connecting portion positioned proximally relative to the hollow tubular member, wherein the connecting portion is configured to acoustically couple the waveguide to a transducer.

Example 5

The ultrasonic instrument of Example 4, wherein the connecting portion is removably coupled to the tubular member.

Example 6

The ultrasonic instrument of Example 5, wherein the connecting portion and the ultrasonic blade are each threadably coupled to the tubular member at opposing ends.

Example 7

The ultrasonic instrument of Example 6, wherein the connecting portion defines a first male threaded portion, wherein the ultrasonic blade defines a second male threaded portion, wherein the tubular member defines a first female threaded portion at a first end thereof, wherein the tubular member defines a second female threaded portion at a second end thereof, wherein the first male threaded portion is configured to threadably engage the first female threaded portion, wherein the second male threaded portion is configured to threadably engage the second female threaded portion.

Example 8

The ultrasonic instrument of Example 7, wherein at least one of the threaded portions is positioned at an anti-node associated with resonant ultrasonic vibrations communicated through the waveguide.

Example 9

The ultrasonic instrument of any one or more of Examples 1 through 8, wherein the tubular member comprises a first end and a second end, wherein the tubular member defines a continuous lumen extending between the first and second ends.

Example 10

The ultrasonic instrument of any one or more of Examples 1 through 9, wherein the acoustic waveguide comprises a plurality of longitudinally spaced annular grooves.

Example 11

The ultrasonic instrument of any one or more of Examples 1 through 10, wherein a first annular groove of the annular grooves has a longer length than a second annular groove of the annular grooves.

Example 12

The ultrasonic instrument of any one or more of Examples 1 through 11, wherein the acoustic waveguide comprises a plurality of opposing, longitudinally spaced notches.

Example 13

The ultrasonic instrument of any one or more of Examples 1 through 12, wherein the end effector further comprises a clamp arm, wherein the clamp arm is configured to pivot relative to the ultrasonic blade to clamp tissue between the clamp arm and ultrasonic blade.

Example 14

The ultrasonic instrument of any one or more of Examples 1 through 13, further comprising a transducer, wherein the transducer is configured to convert electrical power into ultrasonic vibrations; wherein the ultrasonic blade is configured to be in acoustic communication with the ultrasonic transducer via the tubular member such that the ultrasonic transducer is operable to drive the ultrasonic blade to vibrate ultrasonically.

Example 15

The ultrasonic instrument of any one or more of Examples 1 through 14, wherein the tubular member comprises titanium.

Example 16

An acoustic waveguide, comprising: (a) a proximal portion configured to be acoustically coupled to a transducer assembly; (b) a distal portion defining an ultrasonic blade; and (c) a middle portion positioned between the proximal and distal portions; wherein at least part of the middle portion is hollow; wherein the proximal and distal portions are each constructed of a solid core shaft of material or combination of materials.

Example 17

The acoustic waveguide of Example 16, wherein the acoustic waveguide is constructed of titanium.

Example 18

The acoustic waveguide of any one or more of Examples 16 through 17, wherein the acoustic waveguide is constructed of aluminum.

Example 19

The acoustic waveguide of any one or more of Examples 16 through 17, wherein the middle portion is constructed of a first material or combination of materials, wherein the proximal and distal portions are each constructed of a corresponding second material or combination of materials, wherein the second material or combination of materials is different than the first material or combination of materials.

Example 20

An ultrasonic instrument comprising: (a) an ultrasonic transducer, wherein the ultrasonic transducer is operable to convert electrical power into ultrasonic vibrations; and (b) an acoustic waveguide in acoustic communication with the ultrasonic transducer such that the ultrasonic transducer is operable to drive the ultrasonic blade to vibrate ultrasonically, wherein the acoustic waveguide comprises: (i) a proximal portion, (ii) a distal portion, and (iii) a middle portion, wherein at least part of the middle portion has a lower average density than the proximal and distal portions.

V. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An ultrasonic instrument comprising:
   (a) a shaft assembly, wherein the shaft assembly comprises an acoustic waveguide; and
   (b) an end effector comprising an ultrasonic blade, wherein the ultrasonic blade is in acoustic communication with the acoustic waveguide, wherein the ultrasonic blade is defined by a solid core shaft of a material or combination of materials;
   wherein the acoustic waveguide comprises a hollow tubular member coupled with the solid core shaft, wherein the hollow tubular member comprises:
   (i) a tubular body including inner and outer wall surfaces, wherein the inner and outer wall surfaces define a wall thickness therebetween,
   (ii) a proximal end,
   (iii) a distal end,
   (iv) a lumen defined by the inner wall surface and extending completely between and through the proximal and distal ends, and
   (v) at least one groove that inwardly projects a portion of both the inner and outer wall surfaces of the tubular body toward the lumen.

2. The ultrasonic instrument of claim 1, wherein the hollow tubular member is removably coupled to the ultrasonic blade.

3. The ultrasonic instrument of claim 2, wherein the hollow tubular member and the ultrasonic blade define a junction when removably coupled to one another, wherein the junction is located at a position corresponding to at an anti-node associated with resonant ultrasonic vibrations communicated through the waveguide.

4. The ultrasonic instrument of claim 2, further comprising a connecting portion positioned proximally relative to the hollow tubular member, wherein the connecting portion is configured to acoustically couple the waveguide to a transducer.

5. The ultrasonic instrument of claim 4, wherein the connecting portion is removably coupled to the tubular member.

6. The ultrasonic instrument of claim 5, wherein the connecting portion and the ultrasonic blade are each threadably coupled to the tubular member at opposing ends.

7. The ultrasonic instrument of claim 6, wherein the connecting portion defines a first male threaded portion, wherein the ultrasonic blade defines a second male threaded portion, wherein the tubular member defines a first female threaded portion at a first end thereof, wherein the tubular member defines a second female threaded portion at a second end thereof, wherein the first male threaded portion is configured to threadably engage the first female threaded portion, wherein the second male threaded portion is configured to threadably engage the second female threaded portion.

8. The ultrasonic instrument of claim 7, wherein at least one of the threaded portions is positioned at an anti-node associated with resonant ultrasonic vibrations communicated through the waveguide.

9. The ultrasonic instrument of claim 1, wherein the at least one groove comprises a plurality of longitudinally spaced annular grooves.

10. The ultrasonic instrument of claim 1, wherein the at least one groove includes first and second annular grooves, wherein the first annular groove has a longer length than the second annular groove.

11. The ultrasonic instrument of claim 1, wherein the acoustic waveguide comprises a plurality of opposing, longitudinally spaced notches.

12. The ultrasonic instrument of claim 1, wherein the end effector further comprises a clamp arm, wherein the clamp arm is configured to pivot relative to the ultrasonic blade to clamp tissue between the clamp arm and ultrasonic blade.

13. The ultrasonic instrument of claim 1, further comprising a transducer, wherein the transducer is configured to convert electrical power into ultrasonic vibrations; wherein the ultrasonic blade is configured to be in acoustic communication with the ultrasonic transducer via the tubular member such that the ultrasonic transducer is operable to drive the ultrasonic blade to vibrate ultrasonically.

14. The ultrasonic instrument of claim 1, wherein the acoustic waveguide comprises:
(i) a proximal portion having a solid core,
(ii) a distal portion having a solid core, and
(iii) a middle portion including the hollow tubular member configured to be disposed between the proximal and distal portions, wherein the proximal portion, middle portion, and the distal portion are separately formed and subsequently coupled.

15. The ultrasonic instrument of claim 14, wherein the middle portion is formed from a different material than the proximal or distal portions.

16. An ultrasonic instrument comprising:
(a) an ultrasonic blade;
(b) an ultrasonic transducer, wherein the ultrasonic transducer is operable to convert electrical power into ultrasonic vibrations; and
(c) an acoustic waveguide in acoustic communication with the ultrasonic blade and the ultrasonic transducer such that the ultrasonic transducer is operable to drive the ultrasonic blade to vibrate ultrasonically, wherein the acoustic waveguide comprises:
(i) a proximal portion having a solid core,
(ii) a distal portion having a solid core, and
(iii) a middle portion including a hollow tubular member, wherein the hollow tubular member comprises:
(A) a tubular body including inner and outer wall surfaces, wherein the inner and outer wall surfaces define a wall thickness therebetween,
(B) opposing proximal and distal ends,
(C) a lumen defined by the inner wall surface and extending completely between and through the proximal and distal ends, and
(D) at least one notch that inwardly projects a portion of both the inner and outer wall surfaces of the tubular body toward the lumen.

17. The ultrasonic instrument of claim 16, wherein the proximal end of the hollow tubular member is removably coupled with the proximal portion of the acoustic waveguide and the distal end of the hollow tubular member is removably coupled with the distal portion of the acoustic waveguide.

18. The ultrasonic instrument of claim 16, wherein the lumen of the hollow tubular member is configured to provide space for material deformation for the at least one notch.

19. An ultrasonic instrument comprising:
(a) a shaft assembly, wherein the shaft assembly comprises an acoustic waveguide; and
(b) an end effector comprising an ultrasonic blade, wherein the ultrasonic blade is in acoustic communication with the acoustic waveguide, wherein the ultrasonic blade is defined by a solid core shaft of a material or combination of materials;
wherein at least a portion of the acoustic waveguide comprises a hollow tubular member coupled with the solid core shaft, wherein the hollow tubular member comprises:
(i) a tubular body having inner and outer wall surfaces, wherein the inner and outer wall surfaces define a wall thickness therebetween,
(ii) a proximal end,
(iii) a distal end,
(iv) a lumen defined by the inner wall surface and extending completely between and through the proximal and distal ends, and
(v) at least one notch or groove that inwardly projects a portion of both the inner and outer wall surfaces of the tubular body toward the lumen, wherein the lumen of the tubular body is configured to provide space for material deformation for the at least one notch or groove.

20. The ultrasonic instrument of claim 1, wherein the at least one notch or groove includes at least one opposing pair of spaced notches.

* * * * *